(12) United States Patent
Moore et al.

(10) Patent No.: US 9,084,575 B2
(45) Date of Patent: Jul. 21, 2015

(54) IVUS SYSTEM WITH ROTARY CAPACITIVE COUPLING

(75) Inventors: Thomas C. Moore, Livermore, CA (US); Robert Zelenka, Milpitas, CA (US)

(73) Assignee: ACIST Medical Systems, Inc., Eden Prairie, MN (US)

( * ) Notice: Subject to any disclaimer, the term of this patent is extended or adjusted under 35 U.S.C. 154(b) by 0 days.

(21) Appl. No.: 13/541,389

(22) Filed: Jul. 3, 2012

(65) Prior Publication Data

US 2012/0271175 A1     Oct. 25, 2012

Related U.S. Application Data

(63) Continuation of application No. 12/465,853, filed on May 14, 2009, now abandoned.

(60) Provisional application No. 61/127,943, filed on May 15, 2008.

(51) Int. Cl.
*A61B 8/14* (2006.01)
*A61B 8/00* (2006.01)
*A61B 8/12* (2006.01)
*H01P 1/06* (2006.01)

(52) U.S. Cl.
CPC .............. *A61B 8/4461* (2013.01); *H01P 1/067* (2013.01); *A61B 8/12* (2013.01); *H01P 1/068* (2013.01)

(58) Field of Classification Search
CPC ...... A61B 8/14; A61B 8/4461; A61B 8/4494; H01P 1/068; H01P 1/063
USPC ......... 600/407, 411, 427, 433, 435, 437, 462, 600/466; 606/14, 19, 254
See application file for complete search history.

(56) References Cited

U.S. PATENT DOCUMENTS

| | | | |
|---|---|---|---|
| 4,674,515 A | 6/1987 | Andou et al. | |
| 4,815,472 A | 3/1989 | Wise et al. | |
| 5,423,797 A | 6/1995 | Adrian et al. | |
| 5,593,415 A | 1/1997 | Adrian | |
| 6,855,143 B2 | 2/2005 | Davison et al. | |
| 2001/0029337 A1 | 10/2001 | Pantages et al. | |
| 2001/0051766 A1 | 12/2001 | Gazdzinski | |
| 2002/0193690 A1 * | 12/2002 | Moore et al. | 600/466 |
| 2004/0051604 A1 * | 3/2004 | Lohr | 333/261 |
| 2006/0007350 A1 * | 1/2006 | Gao et al. | 348/373 |

* cited by examiner

*Primary Examiner* — Unsu Jung
*Assistant Examiner* — Michael N Fisher
(74) *Attorney, Agent, or Firm* — Fredrikson & Byron, P.A.

(57) ABSTRACT

An imaging system comprises a catheter having a lumen, a rotatable imaging probe within the catheter lumen including a distal transducer and first and second conductors coupled to the transducer, and a coupler that couples the rotatable first and second conductors to non-rotatable third and fourth conductors, respectively. The coupler includes a rotary capacitive coupler.

12 Claims, 14 Drawing Sheets

$d_{drum}$: Drum Separation Distance

IVUS SYSTEM WITH ROTARY CAPACITIVE COUPLING

PRIORITY CLAIM

The present application is a continuation of U.S. nonprovisional application Ser. No. 12/465,853, filed May 14, 2009, which claims the benefit of U.S. Provisional Application Ser. No. 61/127,943, filed May 15, 2008.

BACKGROUND OF THE INVENTION

The present invention generally relates to rotary couplers. The present invention more specifically relates to a capacitively coupled rotary coupler for use in a minimally invasive imaging catheter and system.

Intravascular catheters such as intravascular ultrasonic (IVUS) catheters enable imaging of internal structures in the body. In particular, coronary IVUS catheters are used in small arteries of the heart to visualize coronary artery disease. An IVUS catheter will, in general, employ at least one high frequency (20 MHz-45 MHz) ultrasonic transducer that creates pressure waves for visualization. At least one transducer is typically housed within a surrounding sheath or catheter member and mechanically rotated for 360° visualization.

The highest frequencies at which commercially available coronary imaging catheters operate are 40 MHz and 45 MHz. These high frequency probes have an axial resolution of approximately 200 microns. An axial resolution of 200 microns is insufficient to resolve structures with size features smaller than 200 microns. For example, thin-cap fibroatheromas having a thin fibrous cap of 65 microns or less in thickness cannot currently be resolved. The concern regarding thin-cap fibroatheromas is that they are prone to rupture. Plaque rupture can lead to thrombus formation and critical blockages in the coronary artery. The ability to reliably identify thin-cap fibroatheromas can aid interventional cardiologists to develop and evaluate clinical treatment strategies in order to reduce post percutaneous coronary intervention morbidity rates. Therefore, IVUS catheters and systems having improved axial resolution capable of more clearly visualizing micron sized features such as vulnerable plaques are needed in the art. The ability for such systems to operate at high transducer frequencies will be important in that effort.

One of the challenges of these minimally invasive imaging systems is coupling the stationary ultrasound transceiver (transmitter/receiver) to the mechanically rotating transducer. Rotary inductive couplers are used in commercially available IVUS systems. However, rotary inductive couplers are non-ideal for very high frequency (30 MHz-300 MHz) operation because of their relatively high series inductance. At such high frequencies, series inductance will result in an insertion loss into a transmission line of the IVUS catheter. Furthermore, the insertion loss increases with increasing ultrasound imaging frequency which degrades system performance. Rotating inductive couplers also exhibit electrical impedance that can vary with rotational position. The variation of impedance with rotational position causes output signal amplitudes to vary with angular positions and further degrades system performance. The present invention addresses these and other issues towards providing imaging catheters having improved resolution and more constant level output.

SUMMARY

In one embodiment, an imaging system comprises a catheter having a lumen, a rotatable imaging probe within the catheter lumen including a distal transducer and first and second conductors coupled to the transducer. The system further includes a coupler that couples the rotatable first and second conductors to non-rotatable third and fourth conductors. The coupler includes a rotary capacitive coupler.

The coupler may comprise a parallel plate capacitor. The coupler may comprise a first parallel plate capacitor that couples the first conductor to the third conductor and a second parallel plate capacitor that couples the second conductor to the fourth conductor or a parallel plate capacitor that couples the first conductor to the third conductor and a cylindrical surface concentric capacitor that couples the second conductor to the fourth conductor.

The coupler may comprise a cylindrical surface concentric capacitor. The coupler may comprise a first cylindrical surface concentric capacitor that couples the first conductor to the third conductor and a second cylindrical surface concentric capacitor that couples the second conductor to the fourth conductor.

The coupler may comprise a conical surface concentric capacitor. The coupler comprises a conical surface concentric capacitor that couples the first conductor to the third conductor and a parallel plate capacitor that couples the second conductor to the fourth conductor, a conical surface concentric capacitor that couples the first conductor to the third conductor and a cylindrical surface concentric capacitor that couples the second conductor to the fourth conductor, or a first conical surface concentric capacitor that couples the first conductor to the third conductor and a second conical surface concentric capacitor that couples the second conductor to the fourth conductor.

The coupler may be within the catheter or outside of the catheter.

In another embodiment, an imaging system comprises a catheter having a lumen and a distal rotatable imaging probe within the catheter lumen including a first transducer, first and second conductors coupled to the first transducer, a second transducer, and third and fourth conductors coupled to the second transducer. The system further includes a rotary capacitive coupler that couples the rotatable first and second conductors to non-rotatable fifth and sixth conductors, respectively, and a rotary inductive coupler that couples the rotatable third and fourth conductors to non-rotatable seventh and eighth conductors, respectively.

The coupler may comprise a parallel plate capacitor. The coupler may comprise a first parallel plate capacitor that couples the first conductor to the third conductor and a second parallel plate capacitor that couples the second conductor to the fourth conductor or a parallel plate capacitor that couples the first conductor to the third conductor and a cylindrical surface concentric capacitor that couples the second conductor to the fourth conductor.

The coupler may comprise a cylindrical surface concentric capacitor. The coupler may comprise a first cylindrical surface concentric capacitor that couples the first conductor to the third conductor and a second cylindrical surface concentric capacitor that couples the second conductor to the fourth conductor.

The coupler may comprise a conical surface concentric capacitor. The coupler comprises a conical surface concentric capacitor that couples the first conductor to the third conductor and a parallel plate capacitor that couples the second conductor to the fourth conductor, a conical surface concentric capacitor that couples the first conductor to the third conductor and a cylindrical surface concentric capacitor that couples the second conductor to the fourth conductor, or a first conical surface concentric capacitor that couples the first conductor to the third conductor and a second conical surface concentric capacitor that couples the second conductor to the fourth conductor.

In a further embodiment, an imaging system comprises a catheter having a lumen, a rotatable imaging probe within the catheter lumen including a distal transducer, and a coupler including a rotary capacitive coupler that couples the rotatable transducer to non-rotatable first and second conductors and a rotary inductive coupler that couples the rotatable transducer to third and fourth non-rotatable conductors.

BRIEF DESCRIPTION OF THE DRAWINGS

The features of the present invention which are believed to be novel are set forth with particularity in the appended claims. The invention, together with further features and advantages thereof, may best be understood by making reference to the following descriptions taken in conjunction with the accompanying drawings, in the several figures of which like reference numerals identify identical elements, and wherein:

DETAILED DESCRIPTION OF THE INVENTION

Figure 1:
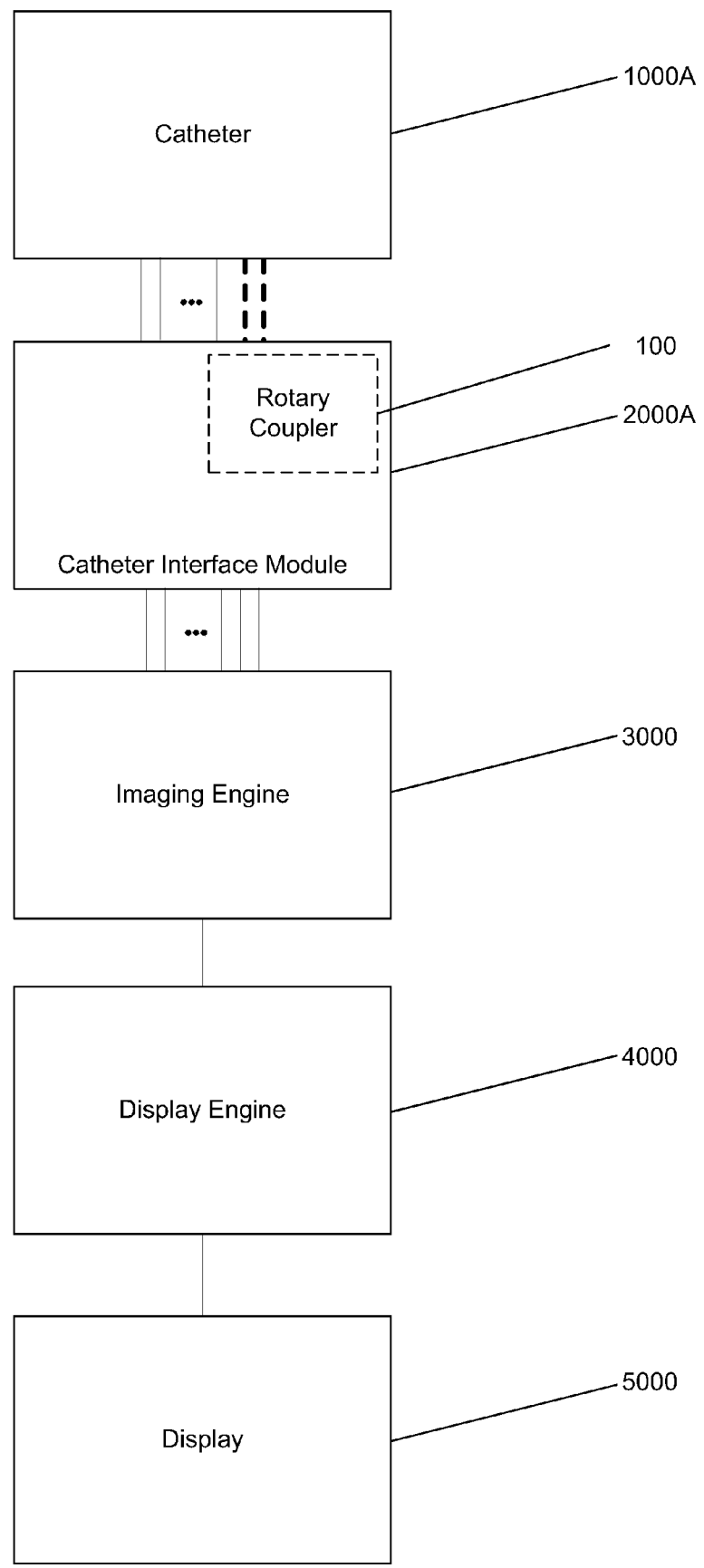
FIG. 1 is a high-level diagram of a catheter-based imaging system comprising a rotary coupler as part of a catheter interface module.

A high-level diagram of the components of a catheter-based imaging system is shown in FIG. 1. A catheter 1000A is coupled mechanically and electrically to a catheter interface module 2000A comprised of a rotary coupler 100. An imaging engine 3000 is in electrical communication with the catheter interface module. Following the imaging engine 3000 is a display engine 4000 and a display 5000.

Figure 2:
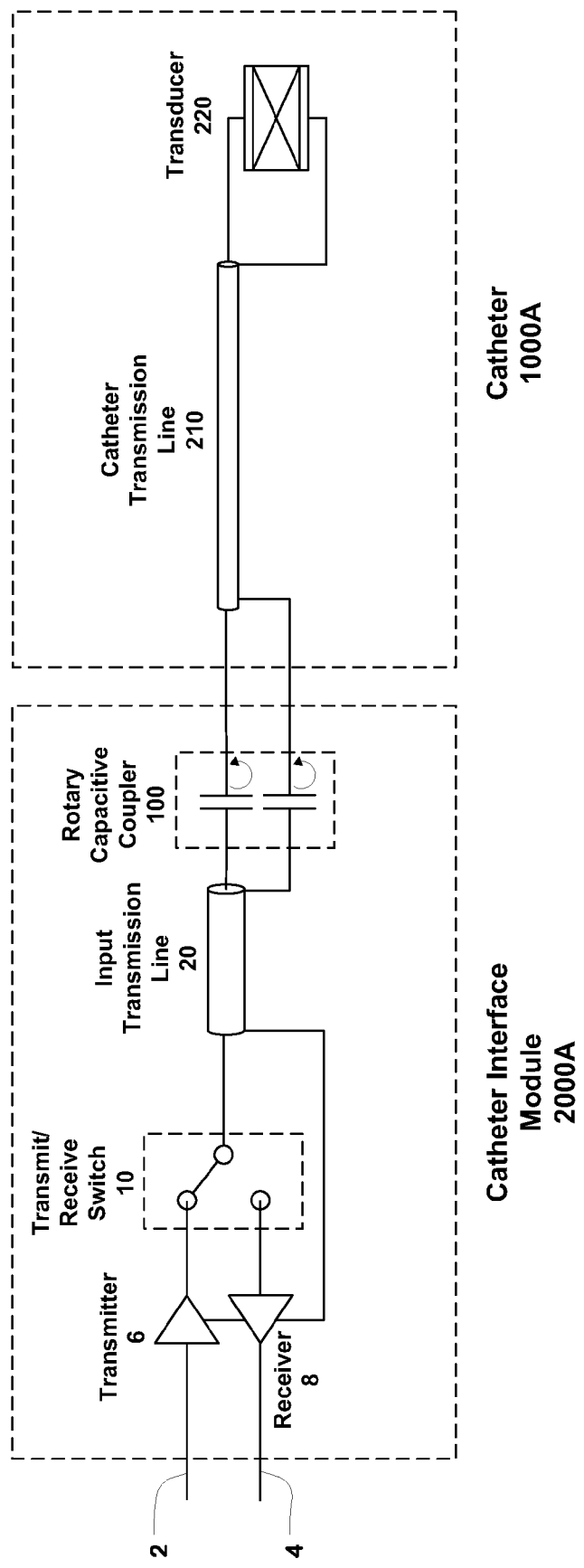
FIG. 2 is a schematic representation of electrical signal paths of a catheter-based imaging system comprising a rotary coupler as part of a catheter interface module.

FIG. 2 shows an electrical schematic representation of the transmit and receive signal paths of a catheter interface module 2000A and catheter 1000A having a primary purpose of coupling a signal from a stationary electrical conduit to a rotating electrical conduit. Diagrams for a rotary capacitive coupler 100 and ultrasonic transducer 220 are shown. In accordance with this embodiment, the rotary capacitive coupler 100 is located outside of the catheter 1000A and within the catheter interface module 2000A.

Figure 3:
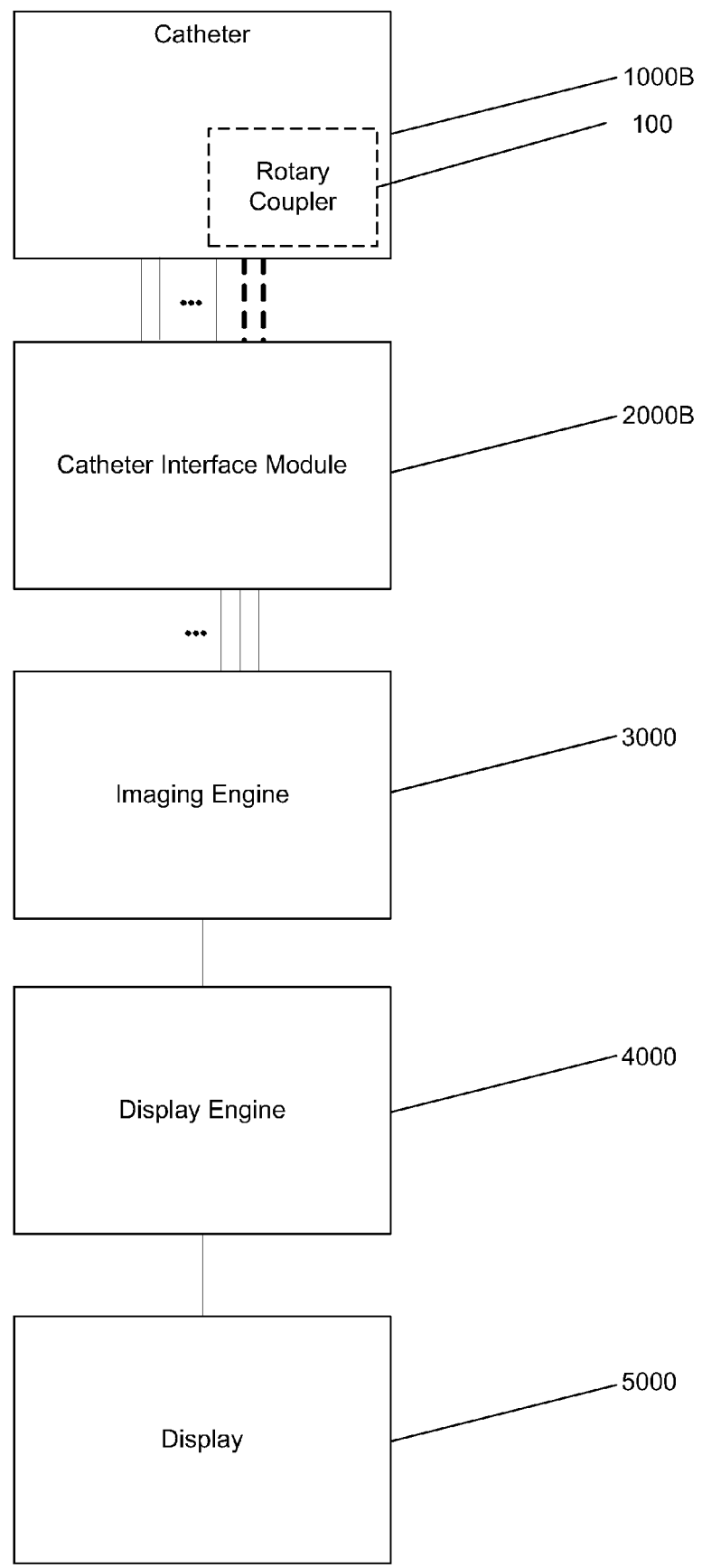
FIG. 3 is a high-level diagram of a catheter-based imaging system comprising a rotary coupler as part of a catheter.

FIG. 3 shows a high-level diagram of the components of another catheter-based imaging system. The components 1000B, 2000B, 3000, 4000, 5000 of the catheter-based based imaging system in FIG. 3 are substantially the same as the components 1000A, 2000A, 3000, 4000, 5000 of the catheter-based imaging system in FIG. 1 and hence, reference characters for like elements are repeated in FIG. 3. However, in this embodiment, a rotary coupler 100 is located in the catheter 1000B.

Figure 4:
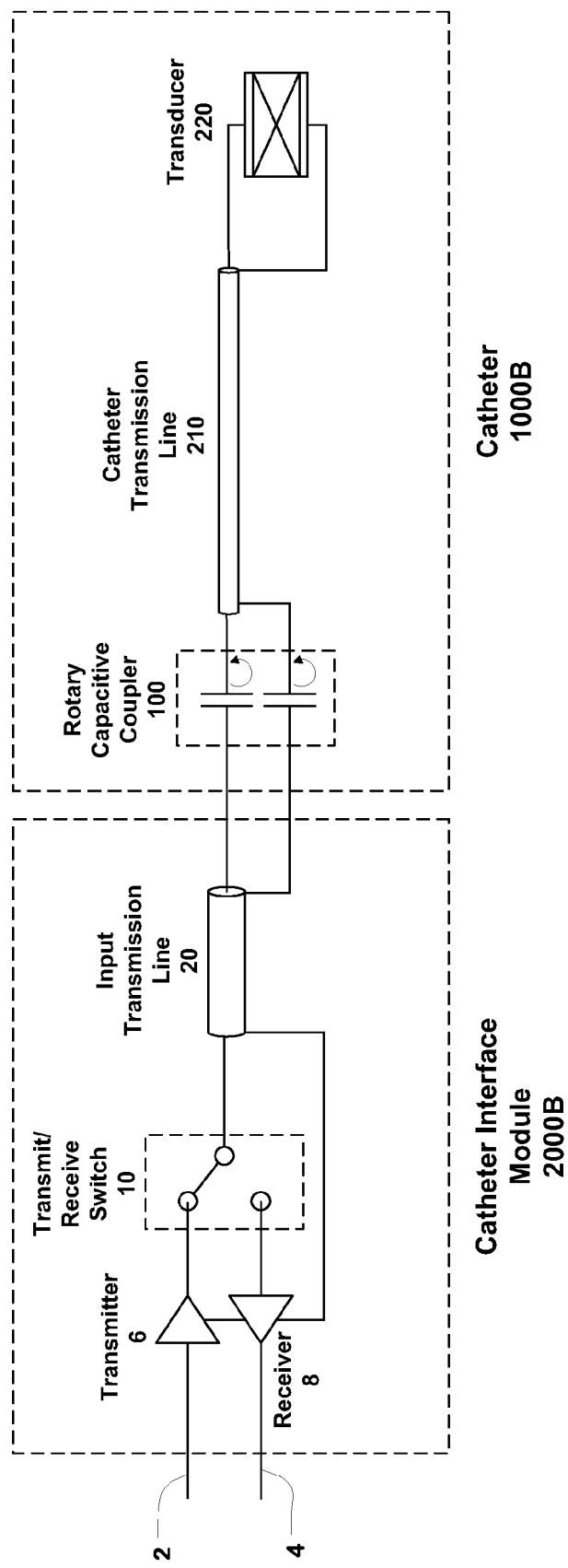
FIG. 4 is a schematic representation of electrical signal paths of a catheter-based imaging system comprising a rotary coupler as part of a catheter.

FIG. 4 is an electrical schematic representation of the system signal paths of the system of FIG. 3 and to the extent that it is the same as the electrical schematic representation in FIG. 2, reference characters for like elements are repeated. However, as may be noted in FIG. 4, the rotary capacitive coupler 100 is located in the catheter 1000B.

Figure 5:
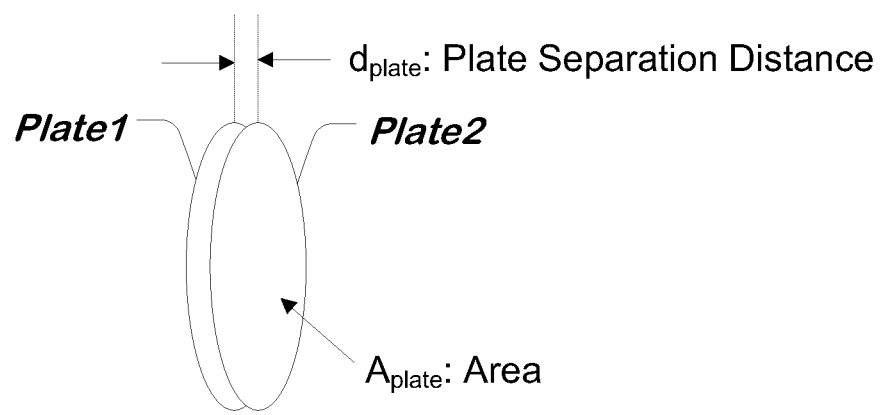
FIG. 5 is a side perspective view of a parallel plate capacitor.
Figure 6:
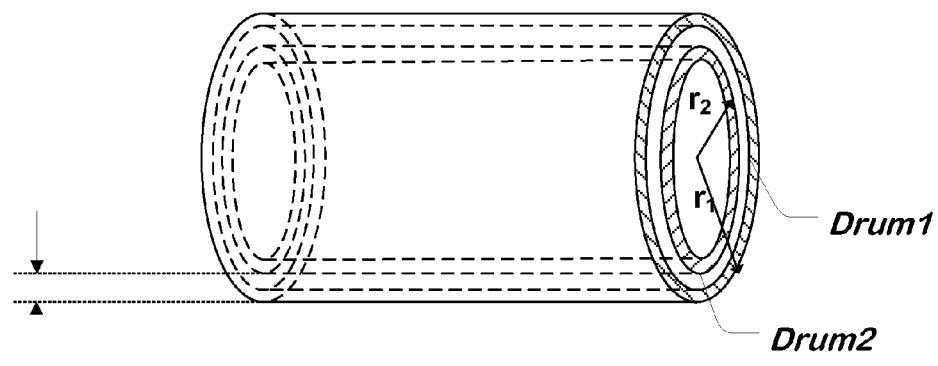
FIG. 6 is a side perspective view of a cylindrical surface concentric capacitor.
Figure 7:
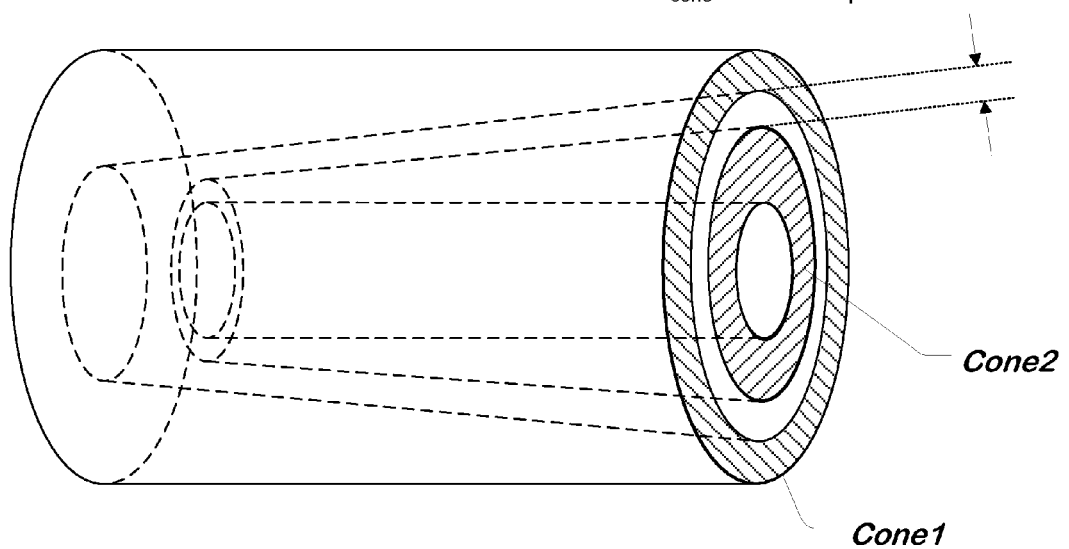
FIG. 7 is a side perspective view of a conical surface concentric capacitor.

FIGS. 5-7 show illustrations of parallel plate and concentric capacitors which may be employed in the various embodiments described hereinafter. FIG. 5 shows a side perspective view of a parallel plate capacitor. The capacitance of the parallel plate capacitor depends on the cross-sectional area $A_{plate}$ and separation distance $d_{plate}$ of two parallel plates Plate1,Plate2 and is closely approximated by $$C = \frac{\varepsilon_0 \varepsilon_r A_{plate}}{d_{plate}}$$

where C is the capacitance in Farads (F), $A_{plate}$ is the area of each plate in square meters (m$^2$), $\varepsilon_r$ is the relative static permittivity or dielectric constant, $\varepsilon_0$ is the permittivity of free space (i.e., 8.854×10$^{-12}$ F/m) and $d_{plate}$ is the separation distance between the plates in meters (m).

FIG. 6 shows a side perspective view of a concentric capacitor comprised of cylindrical surfaces. The capacitance per unit length of the cylindrical surface concentric capacitor depends on the radii $r_1$, $r_2$ of the drums (or cylinders) Drum1, Drum2 and is approximately $$\frac{2\pi\varepsilon_0\varepsilon_r}{\ln\left(\frac{r_1}{r_2}\right)}.$$

The reactive impedance experienced by a signal of frequency f across the capacitor or is $|xc|=(2\pi f c)^{-1}$.

FIG. 7 shows a side perspective view of a concentric capacitor comprised of conical surfaces. The capacitance of the conical surface concentric capacitor is similar to the capacitance of the cylindrical surface concentric capacitor. The cone separation distance $d_{cone}$ can be varied by adjusting the relative axial position of the cones Cone1, Cone2. The ability to adjust the separation distance enables variation of the capacitance.

For a given capacitance C of the capacitors of FIGS. 5-7, the reactive impedance $|Xc|$ decreases as frequency f increases. Insertion loss for a rotary capacitive coupler decreases with increasing frequency and increasing capacitance. Capacitance can be increased by increasing the relative static permittivity of the capacitor gap filler material, increasing the surface area of the capacitor surfaces, or decreasing the gap between capacitor surfaces. The gap filler material can be a variety of materials including air, polyethylene, quartz, or glass. The benefit of decreased insertion loss to imaging performance is improved axial resolution of the imaging system due to use of higher transducer frequencies.

Figure 8:
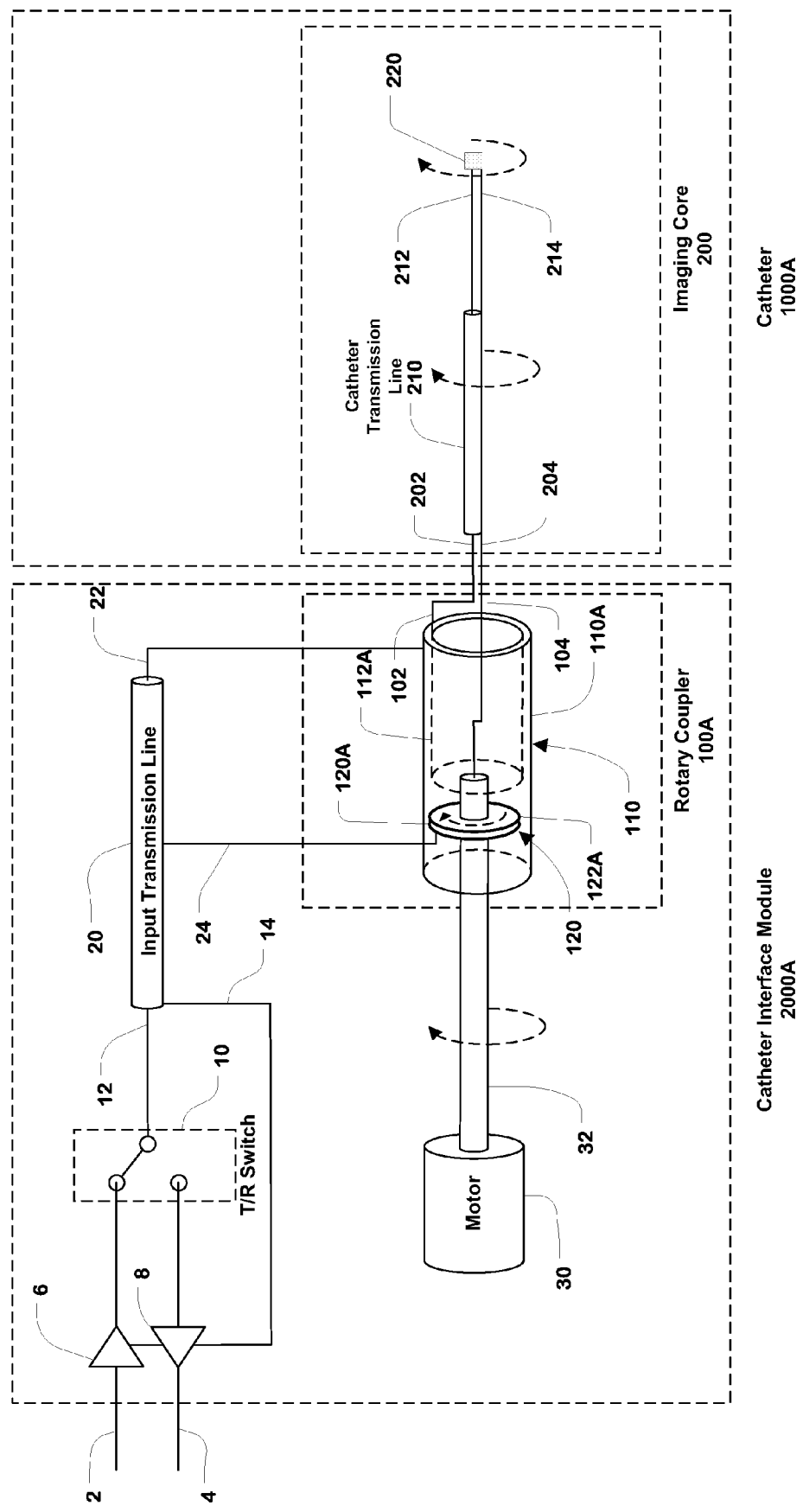
FIG. 8 is a diagram of a rotary capacitive coupler located in a catheter interface module and comprised of a cylindrical surface concentric capacitor and a parallel plate capacitor.
Figure 9:
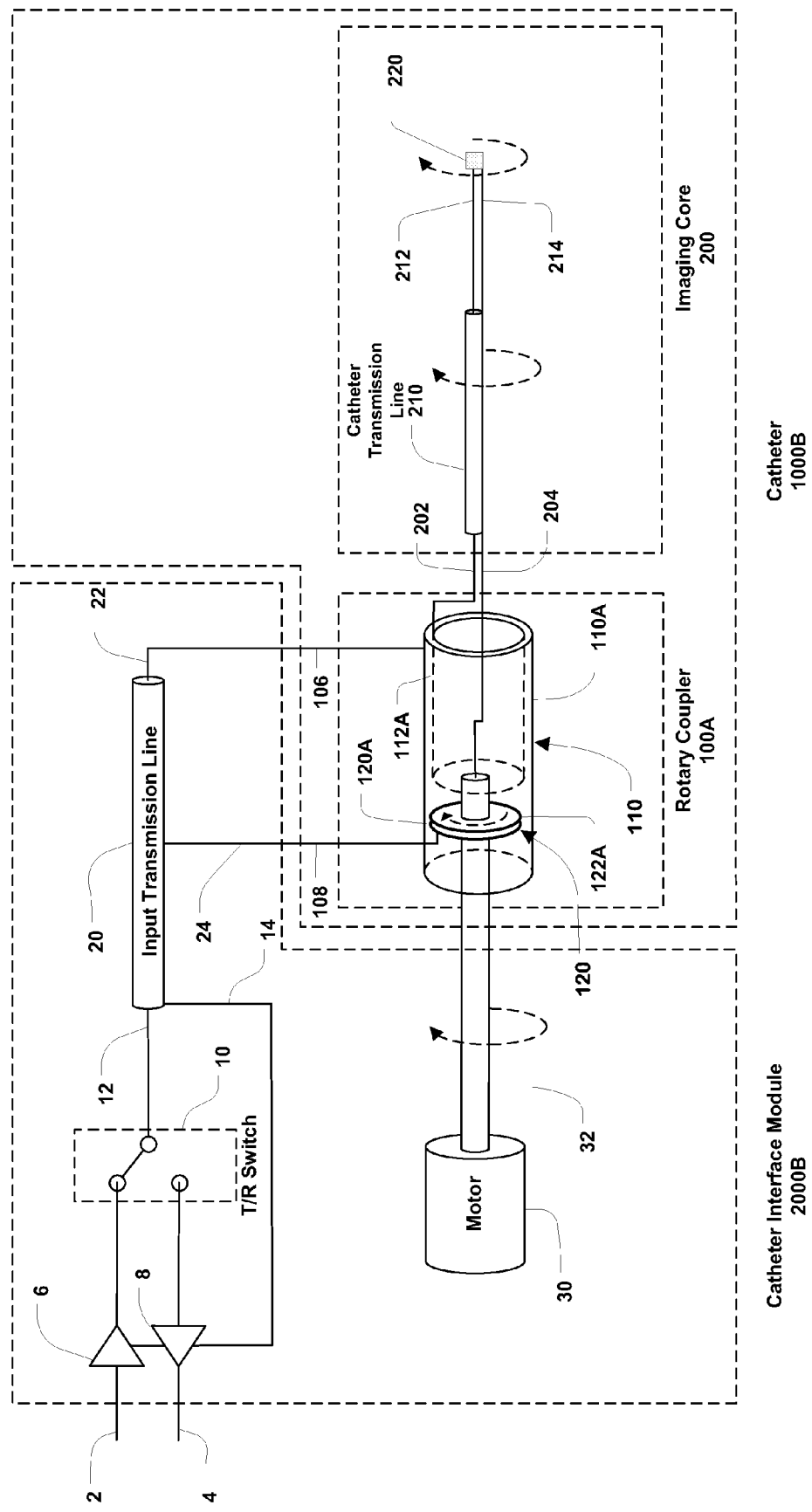
FIG. 9 is a diagram of a rotary capacitive coupler located in a catheter and comprised of a cylindrical surface concentric capacitor and a parallel plate capacitor.

FIGS. 8 and 9 illustrate separate embodiments of an IVUS system and catheter wherein a rotary capacitive coupler can either be located in a catheter interface module (FIG. 8) or a catheter (FIG. 9). FIG. 8 shows a diagram of a catheter interface module 2000A and catheter 1000A wherein a rotary capacitive coupler 100A is located in the catheter interface module. The rotary capacitive coupler comprises a cylindrical surface concentric capacitor 110 including concentric drums 110A, 112A and a parallel plate capacitor 120 including plates 120A, 122A, respectively. The advantage of this design is that the fixed non-rotatable drum 120A acts as a shield to electrical noise for the parallel plate capacitor.

A high frequency (>40 MHz) signal travels from a send path 2 to the center conductor 212 of a catheter transmission line 210 in the catheter imaging core, through an ultrasound transducer 220, back through a transmission line shield 214, and finally back to the return path conductor 4. The imaging core 200 components 212,214,220 rotate inside a catheter sheath by means of a drive motor 30. The imaging core conductors 212,214 are electrically loaded by a transducer 220. The rotary coupler 100A comprising the cylindrical surface concentric capacitor 110 and the parallel plate capacitor 120 is used to electrically couple the fixed and rotating components. A drive shaft 32 is mechanically coupled to the rotating drum 112A and rotating plate 122A.

When operating in a send mode the send signal along conductor 2 passes through a transmit/receive (T/R) switch 10 to the conductor 12 leading to an input transmission line 20. The outputs of the input transmission line 20 are a send signal conductor 22 and a return signal conductor 24. The conductors 22,24 are the inputs to the rotational coupler. The rotary coupler transfers (or couples) electrical signals between the send signal conductor 22 and the proximal end of the catheter transmission line 210 center conductor 202. The rotary coupler also transfers electrical signals between the return signal conductor 24 and the proximal end of the catheter transmission line shield 204. This is achieved with two capacitors.

The send coupling capacitor 110 comprises concentric drums 110A,112A. The return coupling capacitor 120 comprises parallel plates 120A,122A. Regarding the two capacitors, fixed components 110A,120A remain stationary while rotating components 112A,122A rotate with the motor 30, drive shaft 32, and catheter imaging core 200. Input transmission line center conductor 22 electrically connects to drum 110A, and the send signal on conductor 22 is coupled to drum 112A which is electrically connected to catheter transmission line center conductor 212. The input transmission line shield 24 electrically connects to the fixed plate 120A, and the signal on conductor 24 gets coupled to rotating plate 122A which is electrically connected to catheter transmission line shield conductor 214. A radiofrequency (RF) connector (not shown) is used to connect conductors 102,104 of the catheter interface module and conductors 202,204 of the catheter. Any RF connector can generally be used, but a subminiature RF connector such as an SMB connector is typically used. Consequently, signals on stationary input transmission line conductors 22,24 get coupled to the rotating catheter transmission line conductors 202,204.

The same rotational coupler serves to couple high frequency (>40 MHz) signals generated by the transducer 220 (from ultrasound reflections) back in the reverse (or return) direction. In the return case, signals generated from the transducer 220 are sent to the receiver 8 through the imaging core conductors 202,204 and input transmission line input-side conductors 12,14. The rotary coupler capacitively couples the signals on the imaging core proximal conductors 202,204 to input transmission line output-side conductors 22,24. The input transmission line 20 outputs the receive signals on input-side conductors 12,14. The signal on conductor 12 is sent to conductor 4 via the T/R switch 10 which would be set for the receive path. Note that the send and receive cases are never allowed to occur simultaneously. A transmit signal is sent to the transducer 220 (with the T/R switch 10 set to send) before the T/R switch 10 is set to receive.

The diagram of a catheter interface module 2000B and catheter 1000B in FIG. 9 is substantially the same as the diagram of the catheter interface module 2000A and catheter 1000A in FIG. 8 and hence, reference characters for like elements are repeated in FIG. 9. A rotary capacitive coupler 100A comprises a cylindrical surface concentric capacitor 110 having concentric drums 110A, 112A and a parallel plate capacitor 120 having parallel plates 120A,122A and is located in the catheter. An RF connector (not shown) is used to connect conductors 22,24 of the catheter interface module and conductors 106,108 of the catheter. A subminiature RF connector such as an SMB connector is typically used. Signals on stationary input transmission line conductors 22,24 are coupled to the rotating catheter transmission line conductors 202,204.

FIGS. 10-13 show various embodiments of rotary capacitive couplers that may be employed in practicing the present invention. The diagrams of the rotary capacitive couplers, drive motor, and drive shaft in FIGS. 10-13 are substantially the same as the diagram of the the rotary capacitive couplers, drive motor, and drive shaft in FIG. 8 and hence, reference characters for like elements are repeated in FIGS. 10-13.

Figure 10:
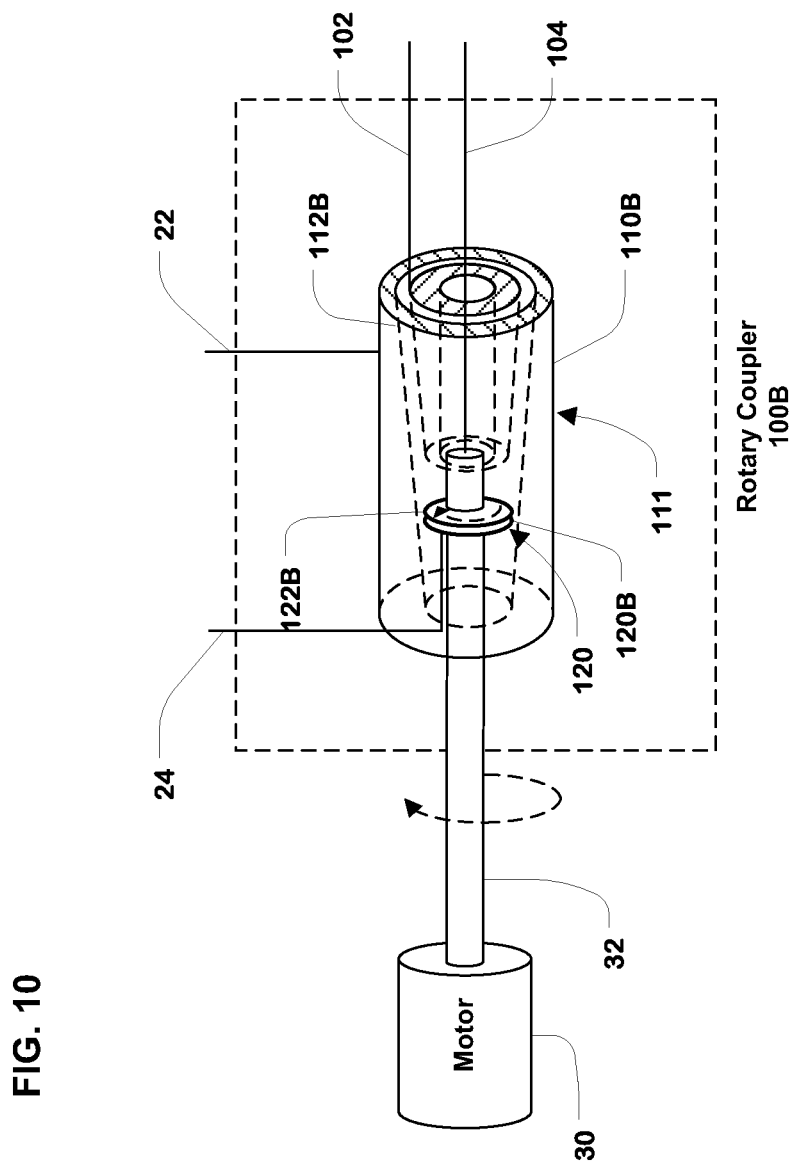
FIG. 10 is a diagram of a rotary capacitive coupler comprised of a conical surface concentric capacitor and a parallel plate capacitor.

The rotary capacitive coupler 100B illustrated in FIG. 10 comprises a conical surface concentric capacitor 111 having concentric conical surfaces 110B,112B and a parallel plate capacitor 120 having plates 120B,122B. The output-side input transmission line conductors 22,24 are electrically connected to the rigidly fixed conical surface 110B and parallel plate 120B. The rotatable conical surface 112B is electrically connected to conductor 102 and mechanically connected to the drive shaft 32. The rotatable parallel plate 122B is electrically connected to conductor 104 and mechanically connected to the drive shaft 32.

Figure 11:
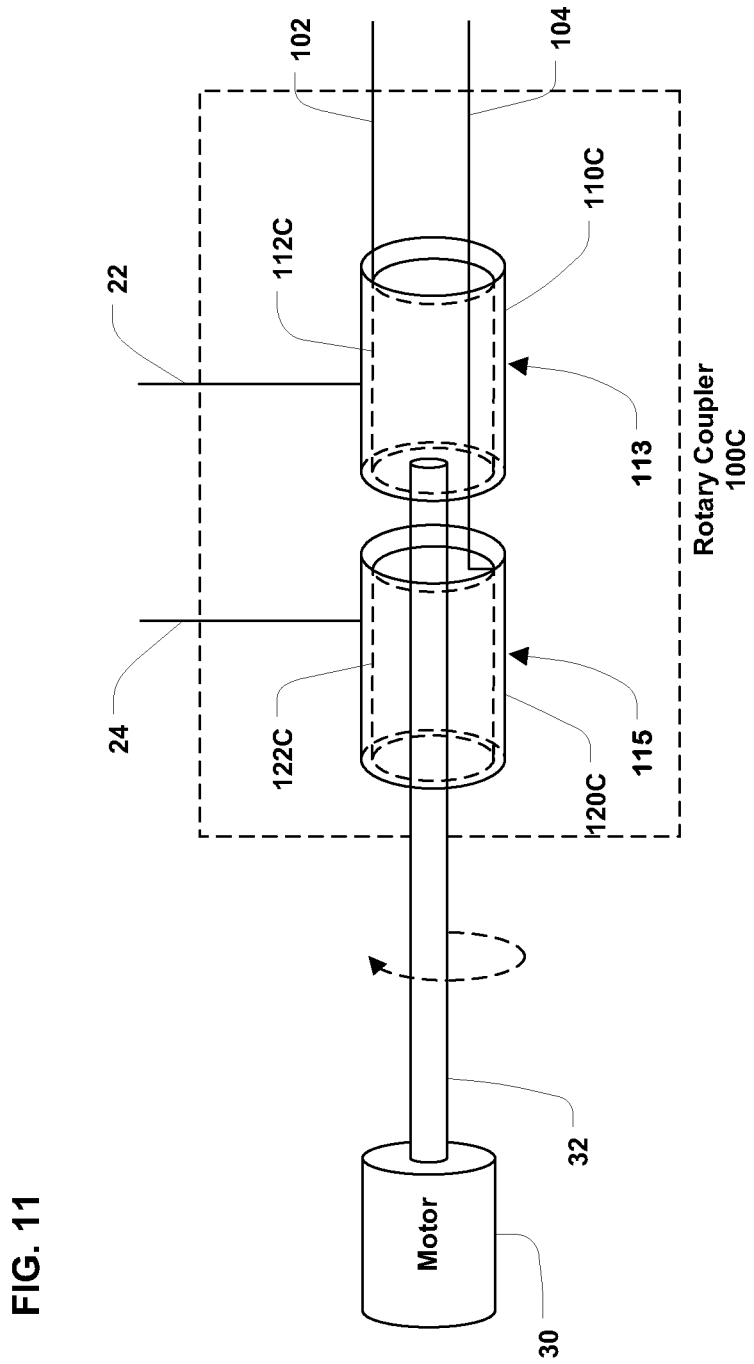
FIG. 11 is a diagram of a rotary capacitive coupler comprised of cylindrical surface concentric capacitors.

FIG. 11 shows a rotary capacitive coupler 100C comprised of two cylindrical surface concentric capacitors 113 and 115 having concentric drums 110C, 112C and 120C, 122C, respectively. The output-side input transmission line conductors 22,24 are electrically connected to the rigidly fixed cylindrical surfaces 110C,120C. The rotatable cylindrical surface 112C is electrically connected to conductor 102 and mechanically connected to the drive shaft 32. The rotatable cylindrical surface 122C is electrically connected to conductor 104 and mechanically connected to the drive shaft 32.

Figure 12:
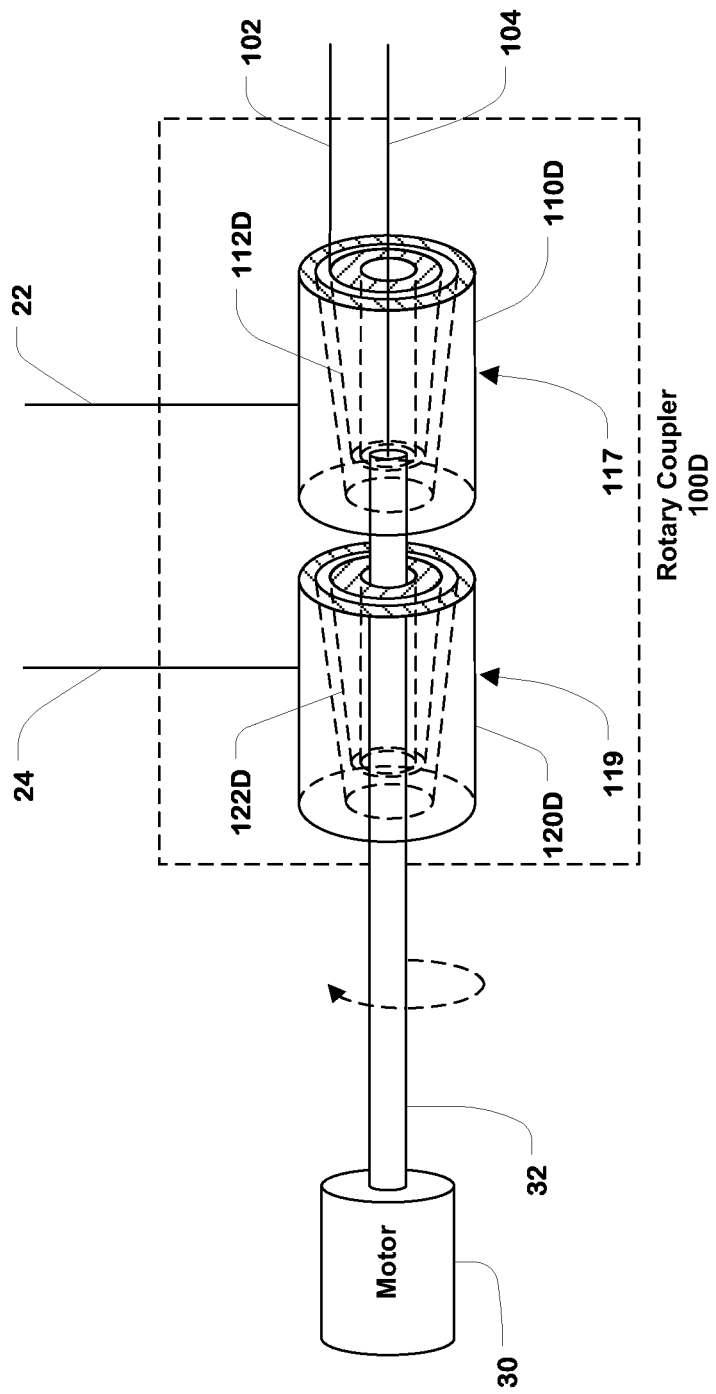
FIG. 12 is a diagram of a rotary capacitive coupler comprised of conical surface concentric capacitors.

FIG. 12 shows a rotary capacitive coupler 100D comprised of two conical surface concentric capacitors 117 and 119 having concentric surfaces 110D, 112D and 120D, 122D, respectively. The output-side input transmission line conductors 22,24 are electrically connected to the rigidly fixed conical surfaces 110D,120D. The rotatable conical surface 112D is electrically connected to conductor 102 and mechanically connected to the drive shaft 32. The rotatable conical surface 122D is electrically connected to conductor 104 and mechanically connected to the drive shaft 32.

Figure 13:
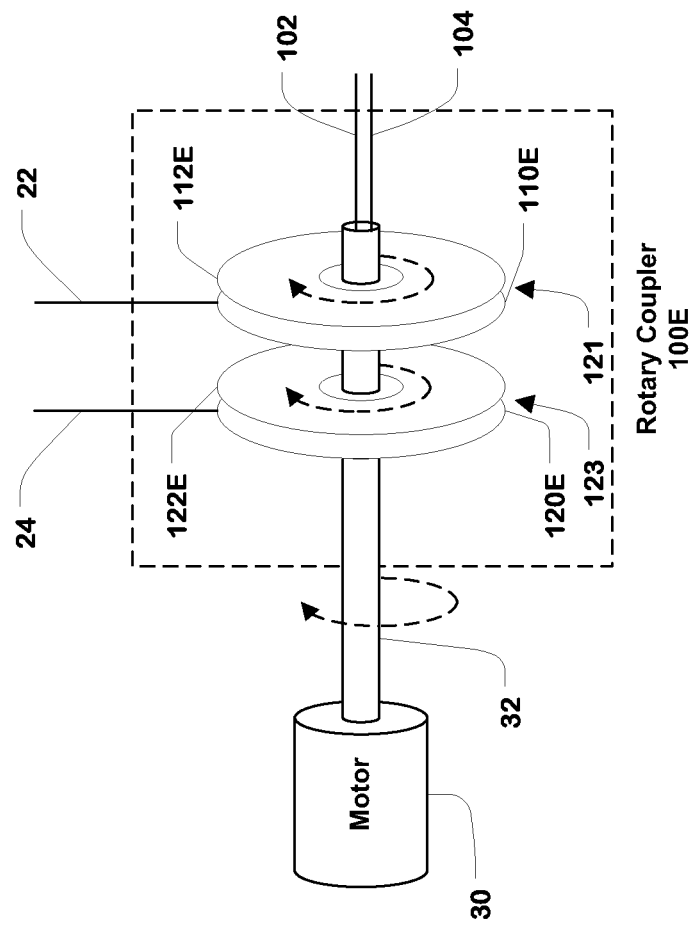
FIG. 13 is a diagram of a rotary capacitive coupler comprised of parallel plate capacitors.

FIG. 13 shows a rotary capacitive coupler 100E comprised of two parallel plate capacitors 121 and 123 having plate pairs 110E, 112E and 120E, 122E, respectively. The output-side input transmission line conductors 22,24 are electrically connected to the rigidly fixed parallel plates 110E,120E. The rotatable parallel plate 112E is electrically connected to conductor 102 and mechanically connected to the drive shaft 32. The rotatable parallel plate 122E is electrically connected to conductor 104 and mechanically connected to the drive shaft 32.

Figure 14:
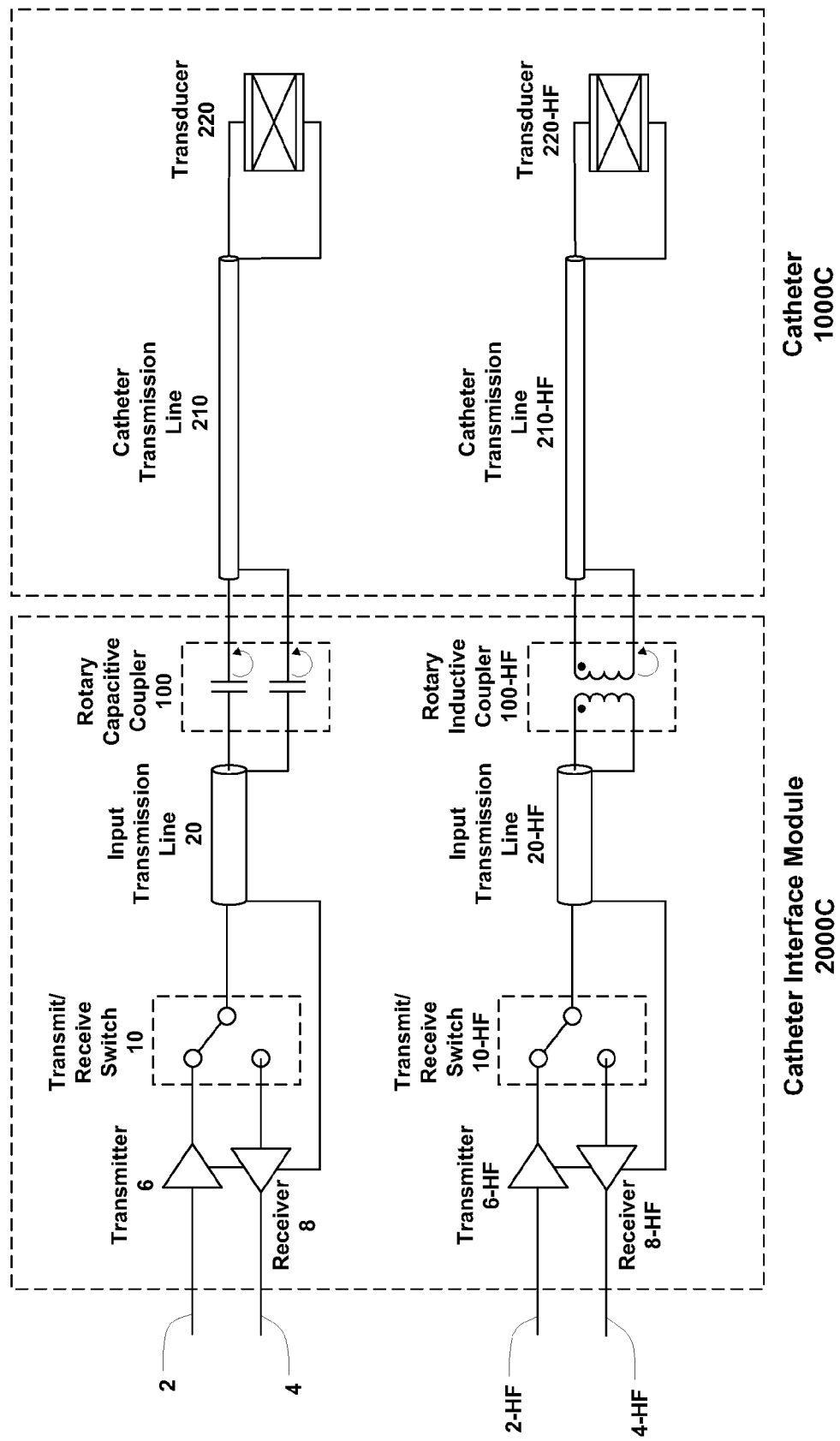
FIG. 14 is a schematic representation of electrical signal paths for a two channel system comprised of a rotary inductive coupler and a rotary capacitive coupler.

FIG. 14 illustrates still another embodiment wherein an IVUS system comprises a rotary capacitive coupler 100 and a rotary inductive coupler 100-HF. A catheter interface module 2000C comprises the rotary inductive coupler 100-HF and the rotary capacitive coupler 100 on a single rotating shaft with two sets of independent electrical connections. The catheter 1000C comprises a high frequency (less than approximately 30 MHz) transducer 220-HF and very high frequency (greater than approximately 30 MHz) transducer 220.

This invention overcomes drawbacks associated with rotary inductive couplers used in minimally invasive, high-frequency IVUS imaging systems and catheters. In particular, rotary capacitive couplers improve system performance by reducing insertion loss and impedance variation with angular position. The rotary capacitive couplers disclosed heretofore comprise parallel plate capacitors, cylindrical surface concentric capacitors, and conical surface concentric capacitors. A parallel plate capacitor comprises a first rigidly fixed plate and a second rotatable plate. A cylindrical surface concentric capacitor comprises a first rigidly fixed cylindrical surface and a second rotatable cylindrical surface. A conical surface concentric capacitor comprises a first rigidly fixed conical surface and a second rotatable conical surface. The exemplary rotary capacitive couplers can be combined for system performance advantages. Furthermore, a rotary inductive coupler and a rotary capacitive coupler can be used in a two channel IVUS system and catheter for high frequency and very high frequency operation.

While particular embodiments of the present invention have been shown and described, modifications may be made, and it is therefore intended to cover in the appended claims, all such changes and modifications which fall within the true spirit and scope of the invention as defined by those claims.

What is claimed is:

1. An imaging system comprising:
   a catheter having a lumen;
   a rotatable imaging probe within the catheter lumen including a distal transducer; and
   a coupler including a rotary capacitive coupler that couples the rotatable transducer to non-rotatable first and second conductors and a rotary inductive coupler that couples the rotatable transducer to third and fourth non-rotatable conductors.

2. The system of claim 1, wherein the rotary capacitive coupler comprises a parallel plate capacitor.

3. The system of claim 1, wherein the rotary capacitive coupler comprises a first parallel plate capacitor that couples the first conductor to the third conductor and a second parallel plate capacitor that couples the second conductor to the fourth conductor.

4. The system of claim 1, wherein the rotary capacitive coupler comprises a parallel plate capacitor that couples the first conductor to the third conductor and a cylindrical surface concentric capacitor that couples the second conductor to the fourth conductor.

5. The system of claim 1, wherein the rotary capacitive coupler comprises a cylindrical surface concentric capacitor.

6. The system of claim 1, wherein the rotary capacitive coupler comprises a first cylindrical surface concentric capacitor that couples the first conductor to the third conductor and second cylindrical surface concentric capacitor that couples the second conductor to the fourth conductor.

7. The system of claim 1, wherein the rotary capacitive coupler comprises a conical surface concentric capacitor.

8. The system of claim 1, wherein the rotary capacitive coupler comprises a conical surface concentric capacitor that couples the first conductor to the third conductor and a parallel plate capacitor that couples the second conductor to the fourth conductor.

9. The system of claim 1, wherein the rotary capacitive coupler comprises a conical surface concentric capacitor that couples the first conductor to the third conductor and a cylindrical surface concentric capacitor that couples the second conductor to the fourth conductor.

10. The system of claim 1, wherein the rotary capacitive coupler comprises a first conical surface concentric capacitor that couples the first conductor to the third conductor and a second conical surface concentric capacitor that couples the second conductor to the fourth conductor.

11. An imaging system comprising:
    a catheter having a lumen;
    a rotatable imaging probe within the catheter lumen including a distal transducer and first and second conductors coupled to the transducer; and
    a rotary capacitive coupler that couples the rotatable first and second conductors to non-rotatable third and fourth conductors, respectively, the rotary capacitive coupler including a parallel plate capacitor mounted within a conical surface concentric capacitor.

12. The system of claim 11, wherein the conical surface concentric capacitor couples the first conductor to the third conductor and the parallel plate capacitor couples the second conductor to the fourth conductor.

* * * * *